(12) United States Patent
Clevenger et al.

(10) Patent No.: US 7,105,306 B1
(45) Date of Patent: Sep. 12, 2006

(54) METHODS AND COMPOSITIONS FOR MODULATING SOMATOLACTOGENIC FUNCTIONS

(75) Inventors: Charles Clevenger, Merion Station, PA (US); Michael A. Rycyzyn, Paoli, PA (US)

(73) Assignee: Trustees of the University of Pennsylvania, Philadelphia, PA (US)

( * ) Notice: Subject to any disclaimer, the term of this patent is extended or adjusted under 35 U.S.C. 154(b) by 332 days.

(21) Appl. No.: 10/049,562

(22) PCT Filed: Aug. 10, 2000

(86) PCT No.: PCT/US00/21789

§ 371 (c)(1),
(2), (4) Date: Jul. 8, 2002

(87) PCT Pub. No.: WO01/13113

PCT Pub. Date: Feb. 22, 2001

(51) Int. Cl.
  *G01N 33/53* (2006.01)
  *C12Q 1/00* (2006.01)
  *C07K 14/00* (2006.01)

(52) U.S. Cl. ............................ 435/7.1; 435/4; 530/350

(58) Field of Classification Search ................ 435/233, 435/7.1
  See application file for complete search history.

(56) References Cited

U.S. PATENT DOCUMENTS 5,523,227 A   6/1996  Bram et al. .............. 435/240.2

FOREIGN PATENT DOCUMENTS

WO    WO 9967288 A1  * 12/1999

OTHER PUBLICATIONS

Bugli et al., Expression Cloning and Biochemical Characterizations of Recombinant Cyclophlin Proteins from *Schistosoma mansoni*, 1998, Protein Expression and Purification, vol. 12, pp. 340-346.*

Ryczyn et al., Role of Cyclophilins in Somatolactogenic Action, 2000, Annals New York Academy of Sciences, vol. 917, pp. 514-521.*

Arkins et al. Somatolactogens, Somatomedins, and Immunity. (1993) J. Dairy Sci. vol. 76, pp. 2437-2450.*

Allain et al., "Characterization of Surface Binding Sites for Cyclophilin B on a Human Tumor T-cell Line", *J. Biol. Chemistry* 1994 269 (24) : 16537-16540.*

Allain et al., "Selective assay for CyPA and CyPB in human blood using highly specific anti-peptide antibodies", *J. Immunological Methods* 1995 178:113-120.*

Denys et al., "Involvement of two classes of binding sites in the interactions of cyclophilin B with peripheral blood T-lymphocytes", *Biochem.* 1998 336:689-697.*

Denys et al., "Distribution of cyclophilin B-binding sites in the subsets of human peripheral blood lymphocytes", *Immunology* 1997 91:609-617.*

Mariller et al., "Involvement of the N-terminal part of cyclophilin B in the interaction with specific Jurkat T-cell binding sites", *Biochemical Journal* 1996 317:571-576.*

Mertani et al., "Cellular Expression of Growth Hormone and Prolactin Receptors in Human Breast Disorders", *Int. J. Cancer Pred. Oncol.* 1998 79:202-211.*

Price et al., "Cyclophilin B trafficking through the secretory pathway is altered by binding of cyclopsporin A", *Proc. Natl. Acad. Sci. USA* 1994 91:3931-3935.*

Price et al., "Human cyclophilin B:A second cyclophilin gene encodes a peptidyl-prolyl isomerase with a signal sequence", *Proc. Natl. Acad. Sci. USA* 1991 88:1903-1907.*

* cited by examiner

*Primary Examiner*—Nashaat T. Nashed
*Assistant Examiner*—Holly Schnizer
(74) *Attorney, Agent, or Firm*—Licata & Tyrrell P.C.

(57) ABSTRACT

Compositions containing cyclophilin B, mutants of cyclophilin B or inhibitors of cyclophilin B and methods of using these compositions to modulate somatolactogenic function are provided.

2 Claims, No Drawings

SEQUENCE LISTING

<160> NUMBER OF SEQ ID NOS: 7

<210> SEQ ID NO 1
<211> LENGTH: 216
<212> TYPE: PRT
<213> ORGANISM: Homo sapiens

<400> SEQUENCE: 1

```
Met Leu Arg Leu Ser Glu Arg Asn Met Lys Val Leu Leu Ala Ala Ala
 1               5                  10                  15

Leu Ile Ala Gly Ser Val Phe Phe Leu Leu Pro Gly Pro Ser Ala
            20                  25                  30

Ala Asp Glu Lys Lys Lys Gly Pro Lys Val Thr Val Lys Val Tyr Phe
            35                  40                  45

Asp Leu Arg Ile Gly Asp Glu Asp Val Gly Arg Val Ile Phe Gly Leu
        50                  55                  60

Phe Gly Lys Thr Val Pro Lys Thr Val Asp Asn Phe Val Ala Leu Ala
 65                  70                  75                  80

Thr Gly Glu Lys Gly Phe Gly Tyr Lys Asn Ser Lys Phe His Arg Val
                85                  90                  95

Ile Lys Asp Phe Met Ile Gln Gly Gly Asp Phe Thr Arg Gly Asp Gly
            100                 105                 110

Thr Gly Gly Lys Ser Ile Tyr Gly Glu Arg Phe Pro Asp Glu Asn Phe
        115                 120                 125

Lys Leu Lys His Tyr Gly Pro Gly Trp Val Ser Met Ala Asn Ala Gly
    130                 135                 140

Lys Asp Thr Asn Gly Ser Gln Phe Phe Ile Thr Thr Val Lys Thr Ala
145                 150                 155                 160

Trp Leu Asp Gly Lys His Val Val Phe Gly Lys Val Leu Glu Gly Met
                165                 170                 175

Glu Val Val Arg Lys Val Glu Ser Thr Lys Thr Asp Ser Arg Asp Lys
            180                 185                 190

Pro Leu Lys Asp Val Ile Ile Ala Asp Cys Gly Lys Ile Glu Val Glu
        195                 200                 205
```

Lys Pro Phe Ala Ile Ala Lys Glu
    210                 215

<210> SEQ ID NO 2
<211> LENGTH: 38
<212> TYPE: DNA
<213> ORGANISM: Artificial Sequence
<220> FEATURE:
<223> OTHER INFORMATION: Description of Artificial Sequence: Synthetic

<400> SEQUENCE: 2
cgggtaccac catgatgaag gtgctccttg ccgccgcc                        38

<210> SEQ ID NO 3
<211> LENGTH: 29
<212> TYPE: DNA
<213> ORGANISM: Artificial Sequence
<220> FEATURE:
<223> OTHER INFORMATION: Description of Artificial Sequence: Synthetic

<400> SEQUENCE: 3
cgctcgagct ccttggcgat gccaaggg                                   29

<210> SEQ ID NO 4
<211> LENGTH: 44
<212> TYPE: DNA
<213> ORGANISM: Artificial Sequence
<220> FEATURE:
<223> OTHER INFORMATION: Description of Artificial Sequence: Synthetic

<400> SEQUENCE: 4
cgggtaccac catgatgaac atcaaaggat cgccatggaa aggg                 44

<210> SEQ ID NO 5
<211> LENGTH: 65
<212> TYPE: DNA
<213> ORGANISM: Artificial Sequence
<220> FEATURE:
<223> OTHER INFORMATION: Description of Artificial Sequence: Synthetic

<400> SEQUENCE: 5
cgctcgagtt actacagatc ctcttctgag atgagttttt gttcgcagtt gttgttgtgg    60
atgat                                                                65

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence: Synthetic

<400> SEQUENCE: 6
aaatacacct tggccgcaga aggtcccgg                                  29

<210> SEQ ID NO 7
<211> LENGTH: 33
<212> TYPE: DNA
<213> ORGANISM: Artificial Sequence
<220> FEATURE:
<223> OTHER INFORMATION: Description of Artificial Sequence: Synthetic

<400> SEQUENCE: 7
gcggccaagg tgtattttga cctacgaatt gga                             33

METHODS AND COMPOSITIONS FOR MODULATING SOMATOLACTOGENIC FUNCTIONS

This invention was supported in part by funds from the U.S. government (NIH Grant No. R01CA69294 and R01DK50771) and the U.S. government may therefore have certain rights in the invention.

BACKGROUND OF THE INVENTION

The somatolactogenic hormones prolactin (PRL) and growth hormone (GH) are necessary for the full growth and maturation of vertebrate species.

Prolactin (PRL) was originally identified as a neuroendocrine hormone of pituitary origin. PRL expression has also been detected in the decidua, breast and T-lymphocytes (Clevenger, C. V. and Plank, T. L. J. Mammary Gland Biol. Neoplasia 1997 2:59–68; Mershon et al. Endocrinology 1995 136:3619–3623; DiMattia et al. Endocrinology 1986 122:2508–2517; Ginsburg, E. and Vonderhaar, B. K. Cancer Res. 1995 55:2591–2595; Gellersen et al. Mol. Endocrinol. 1994 8:356–373; Clevenger et al. Proc. Natl. Acad. Sci. USA 1990 87:6460–6464; Montogomery et al. Biochem. Biophys. Res. Commun. 1987 145:692–698). A primary function of this hormone lies within the breast. However, functional pleiotropism of this peptide with regard to reproduction, osmoregulation and behavior has also been recognized (Nicoll, C. S. Handbook of Physiology; Section 7: Endocrinology, pp. 253–292, Washington, D.C.: American Physiology Society. 1974). Several lines of evidence have also indicated an immunoregulatory role for this peptide (Clevenger et al. Journal of Endocrinology 1998 157: 187–197; Weigent, D. A. Pharmacol. Ther. 1996 69:237–257). Structural analysis of PRL has revealed it to be related to members of the cytokine/hematopoietin family which also includes growth hormone, erythropoietin, granulocyte-macrophage colony stimulating factor (GM-CSF) and interleukins 2–7 (Bazan, J. F. Immunol. Today 1990 11:350–354)

The pleiotropic actions of PRL are mediated through its receptor (PRLr), a member of the superfamily of type I cytokine receptors. PRLr is present on numerous tissues including mammary epithelia, T and B lymphocytes and macrophages (Dardenne et al. Endocrinology 1994 134: 2108–2114; Pellegrini et al. Mol, Endocrinol. 1992 6:1023–1031). Acting through its receptor, PRL signaling stimulates cell proliferation, survival and cellular differentiation in a tissue- and microenvironment-dependent manner. In the mammary and immune systems, PRL is believed to act at the endocrine, paracrine, and autocrine levels in regulating T-lymphocyte proliferation and survival (Gala, R. R. PSEBM 1991 198:513–527; Yu-Lee, L. Y. Proceedings of the Society for Experimental Biology and Medicine 1997 215:35–52; Kooijman et al. Adv. Immunol. 1996 63:377–454; Prystowski, M. B. and Clevenger, C. V. Immunomethods 1994 5:49–55) and the terminal maturation of mammary tissues (Kelly et al. Rec. Prog. Horm. Res. 1993 48:123–164; Shiu et al. Rec. Prog. Horm. res. 1987 43:277–289). PRL is also believed to act as both an endocrine and autocrine/paracrine progression factor for mammary carcinoma in both rodents and humans (Welsch, C. W. Cancer Res. 1985 45:3415–3443; Welsch, C. W. and Nagasawa, H. Cancer Res. 1977 37:951–963; Manni et al. Cancer Res. 1986 37:951–963; Malarkey et al. J. Clin. Endocrinol. Metab. 1983 56:673–677; Clevenger et al. Am. J. Pathol. 1995 146:1–11; Fields et al. Lab. Invest. 1993 68:354–360; Ormandy et al. J. Clin. Endocrinol. Metab. 1997 82:3692–3699; and Mertani et al. Int. J. Cancer 1998 79:202–22).

Pleiotropic actions of GH are also largely mediated through a type I cytokine receptor, GHr.

Ligand-induced dimerization of PRLr and GHr activates several associated signaling cascades including the Jak-Stat, Ras-Raf, and Fyn-Vav pathways (Campbell et al. Proc. Natl. Acad. Sci. USA 1994 91:5232; Clevenger et al. J. Biol. Chem. 1994 269:5559; Clevenger et al. Mol. Endocrinol. 1994 8:674; Clevenger et al. J. Biol. Chem. 1995 270: 13246). However, studies indicate that both PRL and GH are internalized via an endosomal-like pathway and transported across the endoplasmic reticulum (ER) and nuclear envelopes (Clevenger et al. Endocrinology 1990 127:3151; Rao et al. J. Cell Physiol. 1995 163:266). This process is referred to as nuclear retrotranslocation. The mechanism of this retrotranslocation, and the nuclear action of these somatolactogenic hormones, however, is not well understood.

Both PRL and GH lack enzymatic activity. These hormones also contain no nuclear translocation signal. Thus, for PRL and GH to act within the nucleus, they must do so through a binding partner or chaperone.

CypB is a member of the cyclophilin family of cistrans peptidyl prolyl isomerases (PPI) (Price et al. Proc. Natl. Acad. Sci. USA 1991 88:1903; Ruhlmann, A. and Nordheim, A. Immunobiol. 1997 198:192; Resch, K. and Szamel, M. Int. J. Immunopharmac. 1997 19:579). This family of proteins was initially identified as the binding partners for the immunosuppressive agent cyclosporine (CsA). CsA interacts with the cyclophilin with high affinity, inhibiting their PPI activity and the action of the phosphatase calcineurin, necessary for NF/AT-transactivated expression of IL-2 (Kronke et al. Proc. Natl. Acad. Sci. USA 1984 81:5214; Liu et al. Cell 1991 55:807; Friedman, J. and Weissman, I. Cell 1991 66:799; McCaffrey et al. J. Biol. Chem. 1993 268:3747; Bram, R. J. and Crabtree, G. R. Nature 1994 371:355; Bram et al. Mol. Cell Biol. 1993 13:4760). Structurally CypB is a β-barrel protein containing both N-terminal ER-leader and putative nuclear translocation signal sequences and C-terminal ER-retention sequences (Allain et al. J. Immunol. Meth. 1995 178:113; Mariller et al. Biochem. Biophys. Acta 1996 1293:31). CypB has been observed in the ER and nucleus, and can be found in appreciable levels in blood (150 ng/ml) and breast milk (Hirada et al. Cell 1990 63:303; Price et al. Proc. Natl. Acad. Sci. USA 1994 91:3931). Cyclophilins, via their PPI activity, facilitate protein folding and have been shown to contribute to the maturation of several proteins, including carbonic anhydrase and the HIV glycoprotein Gag (Taylor et al. Prog. Biophys. Molec. Biol. 1997 67:155; Streblow et al. Virology 1998 245:197). Despite these insights, the physiologic function of CypB has remained uncertain.

It has now been found that cyclophilin B (CypB) interacts specifically with somatolactogenic hormones, PRL and GH, as a chaperone mediating the transport, maturation and/or function of these proteins.

SUMMARY OF THE INVENTION

An object of the present invention is to provide methods of modulating somatolactogenic function in an animal comprising administering to the animal an effective amount of a composition containing cyclophilin B or a mutant or inhibitor thereof.

Another object of the present invention is to provide compositions for modulating somatolactogenic function in an animal comprising cyclophilin B or a mutant or inhibitor thereof and a pharmaceutically acceptable vehicle.

Another object of the present invention is to provide a method of identifying compounds which inhibit somatolactogenic functions associated with PRL and GH which comprises assessing the ability of a test compound to inhibit the interaction of cyclophilin B with PRL or GH.

Yet another object of the present invention it to provide methods and reagents for diagnosing diseases associated with somatolactogenic functions in patients by detecting levels of cyclophilin B in the patients.

DETAILED DESCRIPTION OF THE INVENTION

Somatolactogenic hormones including GH and PRL have been implicated in the development of breast and prostate cancer, growth, and in the immune response. It has now been found that the co-administration of wild-type CypB with somatolactogenic hormones including GH and PRL augments the function of these proteins. Further, it has been found that the generation of appropriate mutants of CypB can inhibit the function of these hormones.

CypB was confirmed to interact directly with somatolactogenic hormones such as PRL and GH. In these experiments, epitope-tagged forms of both proteins were expressed by recombinant techniques and purified to >95%. Co-immunoprecipitation studies performed on the admixed proteins revealed that the introduction of either reducing agent or divalent cation facilitated the direct interaction of CypB with PRL. The addition of CsA, at a therapeutic concentration, was found to enhance the interaction approximately ten-fold, indicating that PRL does not interact with the PPI pocket in CypB that engages CsA. Instead, additional experiments with GST-CypB chimera indicate that PRL binds to the C-terminus of CypB. A recombinant form of the highly homologous cyclophilin family member CypA failed to interact with PRL, further confirming the specific nature of the CypB-PRL interaction. Additional in vivo confirmation of the CypB-PRL interaction was obtained by the direct co-immunoprecipitation of PRL with CypB from human serum, and the binding of serum PRL to a sepharose-conjugated, recombinant CypB.

The effect of exogenous CypB on PRL-driven proliferation was examined with the rat Nb2 T-cell and the human T47D breast cancer line. In response to exogenous PRL, Nb2 cells demonstrate dose-dependent growth (Gout et al. Cancer Res. 1980 40:2437). The addition of CypB into the PRL-containing Nb2 culture medium resulted in up to an eight-fold enhancement of PRL-driven growth as compared to Nb2 cultures that received only PRL. This dose-dependent biphasic effect was most prominent at physiologic concentrations (5–10 mM) of CypB and PRL (50 pM) found in human serum. Similar proliferative responses were observed with the T47D line. The co-addition of CypA into Nb2 cell cultures did not result in any potentiation PRL-driven growth. To determine the effect of CypB on cellular growth driven by the larger family of cytokines, to which PRL belongs, proliferation driven by interleukin-2 (IL-2), IL-3 and GH was examined. Neither IL-2- nor IL-3-driven proliferation was altered by the addition of varying concentration of CypB, whereas physiological concentrations of CypB enhanced GH-driven proliferation forty-fold as compared to cultures receiving similar concentrations of GH alone. Thus, as demonstrated herein somatolactogenic function is significantly potentiated in a synergistic manner by physiologic concentrations of CypB.

Experiments were performed to examine the ability of CypB to enhance nuclear retrotranslocation of PRL, and thereby PRL-driven proliferation. Indirect immunofluorescence of T47D human breast cancer cells labeled with an anti-PRL antibody has been documented to produce a diffuse, speckled pattern of cytosolic immunofluorescence in the majority of cells, consistent with the internalization of PRL into endosomal-like vesicles (Perrot-Applanat et al. J. Cell Sci. 1997 110:1123). In these experiments, however, inclusion of the co-mitogen epidermal growth factor (EGF) into the defined T47D culture medium induced demonstrable anti-PRL immunofluorescence over approximately 10% of the T47D nuclei. These findings are consistent with previous reports in an L2 cloned T-cell line, that revealed a requirement for co-mitogenic stimulation before appreciable nuclear retrotranslocation of PRL was detectable (Clevenger et al. Science 1991 253:77; Clevenger et al. Proc. Natl. Acad. Sci. 1990 87:6460). These experiments also demonstrated that nuclear retrotranslocation of PRL was significantly enhanced by inclusion of CypB into this defined medium, resulting in 95–100% of the T47D nuclei exhibiting anti-PRL immunofluorescence. These data have been confirmed at the biochemical level by the demonstration of intranuclear PRL-CypB complexes by co-immunoprecipitation analysis. These data therefore indicate that CypB acts as a reverse chaperone, facilitating the retrotranslocation of PRL in to the nucleus.

Examination of the amino acid sequence of CypB (GenBank Accession Number NM 000942; SEQ ID NO: 1) revealed a putative nuclear translocation signal in its amino-terminus that is absent in CypA. The role of this sequence in the CypB-mediated retrotranslocation of PRL, and its associated enhancement of growth was tested by mutagenic approaches. The putative nuclear localization sequence of CypB was deleted in the mutant CypB-NT. Comparison of purified wild-type CypB and CypB-NT revealed identical levels of PPI activity, confirming that the mutant protein was appropriately folded and bioactive. Deletion of the nuclear localization sequence did not affect the interaction of PRL with the CypB-NT. However, inclusion of CypB-NT into T47D culture medium did not enhance the nuclear retrotranslocation of PRL, as illustrated by a complete absence of detectable anti-PRL immunofluorescence in any nucleus. CypB also failed to enhance PRL-induced proliferation, despite its ability to interact with PRL. Taken together, these data indicate a role of the N-terminus of CypB in the nuclear retrotransport of PRL and link this to the CypB-associated potentiation of PRL-induced proliferation.

Three additional mutants have also been generated. These include a CypB mutant which lacks the carboxy terminus, referred to as CypB-AIAKE, and two point mutations with the enzymatic pocket (R63A and F68A) of CypB rendering it enzymatically inactive. These mutants are also expected to alter somatolactogenic action.

The present invention relates to methods and compositions for modulating somatolactogenic functions via this interaction of CypB with somatolactogenic hormones. In one embodiment of the present invention, a composition comprising CypB in a pharmaceutically acceptable vehicle can be administered to an animal in an amount effective to augment the function of somatolactogenic hormones including GH and PRL. Specifically, compositions comprising CypB can be used to enhance the immunostimulatory properties of GH and PRL in the treatment of immunosuppression (i.e. conditions such as HIV). Co-administration of CypB can also be used to augment the action of GH in the treatment of short-stature, muscle wasting, and osteoporosis.

Alternatively, a composition comprising a mutant of CypB with dominant negative action such as CypB-NT or an inhibitor of CypB that interferes with its effects with the somatolactogenic hormones and a pharmaceutically acceptable vehicle can be administered to an animal in an amount effective to block the action of PRL and GH. Compositions comprising a CypB mutant or inhibitor of CypB interaction with somatolactogenic hormones can be used in the treatment of breast and prostate cancer, and in the treatment of conditions associated with excess PRL or GH such as pituitary adenomas which can lead to hyperprolactinemia or gigantism/acromegaly. Certain pathologic conditions including, but not limited to, HIV and cancer, can alter the body's levels of CypB thereby resulting in an immunosuppressed state. Thus, compositions of the present invention can also be used in the treatment of these immunosuppressed states.

Appropriate doses of CypB and mutants or inhibitors thereof effective in augmenting or inhibiting somatolactogenic hormones to be administered to animals can be determined based upon data from cell culture experiments such as those described herein. Determination of effective doses from such data is performed routinely by those of skill. In a preferred embodiment, CypB and mutants thereof are administered intravenously or intramuscularly. When used to augment somatolactogenic function, it is preferred that the dosage of CypB administered result in a serum concentration level of CypB similar to normal healthy individuals, i.e. 100–150 ng/ml. To inhibit somatolactogenic function in an animal via administration of a mutant CypB or an inhibitor, higher serum concentrations are preferred. Pharmaceutically acceptable vehicles for use in compositions of the present invention are also well known in the art.

Also provided in the present invention is a method of identifying potential new drugs which inhibit somatolactogenic functions by identifying test compounds which inhibit the interaction of CypB with somatolactogenic hormones such as PRL or GH. Test compounds which inhibit the interaction of CypB with somatolactogenic hormones are expected to inhibit somatolactogenic functions. Thus, such test compounds should be useful as drugs in the treatment of breast and prostate cancer and conditions associated with excess PRL or GH. In one embodiment, test compounds with this inhibitory activity are identified in accordance with cell culture methods described herein. However, as will be obvious to those of skill in the art upon this disclosure, more rapid screening assays to identify compounds which inhibit this interaction can also be developed.

The present invention also relates to a method and reagent for use in diagnosing diseases associated with abnormal somatolactogenic functions. In these methods, the level of cyclophilin B in a biological sample obtained from a patient is determined. In one embodiment, levels are determined via an immunoassay using an anti-cyclophilin B antibody. Preferably, the biological sample comprises blood, serum or plasma. The levels of cyclophilin B determined in the patient are then compared to levels of cyclophilin B in biological samples of normal individuals. Levels of cyclophilin B in the patient which are lower than levels in normal individuals are indicative of diseases or conditions wherein somatolactogenic function must be augmented. Levels of cyclophilin B in the patient which are higher than levels of cyclophilin B in normal individuals are indicative of diseases or conditions wherein somatolactogenic function must be inhibited.

The following nonlimiting examples are provided to further illustrate the present invention.

EXAMPLES

Example 1

Generation of CypB DNA Constructs and Protein

Full length CypB DNA was generated by PCR from an insert isolated in a yeast two-hybrid screen using specific primers containing Kpn1 and Xho1 sites (5'–3-): CGGG-TACCACCATGATGAAGGTGCTCCTTGCCGCCGCC (SEQ ID NO: 2) and CGCTCGAGCTCCTTGGCGATGC-CAAAGGG (SEQ ID NO: 3), with the forward primer containing a Kozak signal sequence. Full length PRL cDNA was generated by PCR using a specific forward primer containing a Kpn1 site and Kozak signal sequence: CGGG-TACCACCATGATGAACATCAAAG-GATCGCCATGGAAAGGG (SEQ ID NO: 4); and a reverse primer containing a Xho1 site and a myc-tag with two stop codons immediately following the tag: CGCTCGAGTTACTACAGATCCTCTTCT-GAGATGAGTTTTTGTTCGCAGTTGTTGTTGTG GAT-GAT (SEQ ID NO: 5). PCR products were purified, digested and subcloned into pAc5/V5-HisA of the *Drosophila* Expression System (InVitrogen). This vector contains a bifunctional V5/His-tag. The sequences of all inserts were confirmed by dideoxynucleotide sequencing. Nineteen micrograms of the vector containing either CypB or PRL was co-transfected with 1 µg of pCoHYDRO into $4 \times 10^6$ *Drosophila* S2 cells by the $CaCl_2$ method and transfectants selected with hygromycin-B as per the manufacturer's instructions (InVitrogen). Myc-tagged PRL was expressed and secreted in the culture supernatant at levels upwards of 10 mg/L. This protein was determined to be functionally bioactive by Nb2 bioassays. His-tagged CypB was expressed intracelullarly and purified as follows: 20 ml cultures containing approximately $2 \times 10^8$ S2 cells were shaken overnight at room temperature at 100 RPM, pelleted and lysed in a minimal NP-40 lysis buffer (50 mM Tris pH 7.8, 10 mM NaCl, 1% NP-40). Lysates (1 ml) were clarified and incubated for 30 minutes with 200 µl of TALON metal affinity resin (Clontech) at room temperature while rotating. Resins was washed 4–5 times with wash buffer (20 mM Tris-HCl pH 8.0, 100 mM NaCl, 10 mM imidazole). Eluted protein was dialyzed overnight at 4° C. against 5 mM HEPES and quantitated with perchloric acid at OD620.

Example 2

Detection of PRL-CypB Complexes by Immunoprecipitation

Purified His-tagged CypB and myc-tagged PRL (10 ng each) were admixed in binding buffer (10 mM Tris pH 7.6, 125 mM NaCl, 10% glycerol) in the presence or absence of 5 mM CaCl2, 1.5 mM 2ME or 50 nM cyclosporin A. Samples were rotated for three hours at room temperature. Complexes were immunoprecipitated by the addition of 1 µg of polyclonal anti-histidine antibody (#sc-803, Santa Cruz Biotech) for one hour followed by roatation for one hour with 50 µl Protein-A beads. Precipiated complexes were separated by 15% SDS-PAGE and transferred to PVDF. Immunoblots were blocked for one hour at room temperature with 5% milk in PBS containing 1% TWEEN-20 (PBST) and immunoblotted with a monoclonal anti-myc antibody (1:1000, mAb 9E10) for one hour. Immunoblots were analyzed by incubation with an anti-mouse secondary antibody conjugated to horseradish peroxidase (1:2000, Boehringer Mannheim) for one hour followed by incubation

Example 3

Use of Nb2 Cell Cultures to Assess CypB Modulation of Somatolactogenic Action Nb2-cells (5×10⁴; PRL-dependent, rat T-lymphoma) were plated in each well of 96 well plates in a defined DMEM-serum free medium (0.1 mM 2-mercaptoethanol, 1% penicillin/streptomycin, and 1% ITS+(Calbiochem)). Cells were rested for 24 hours at 37° C. in this defined medium in the absence of PRL before the addition of 5–500 pM PRL (either as human pituitary isolated PRL, National Hormone and Pituitary Program, NIDDK; recombinant human PRL from *E. coli*, Genzyme; or recombinant human PRL from *Drosophila* S2 cells) alone or premixed with 1–2000 fold excess of purified CypB. Parallel studies were performed using human pituitary-derived GH (National Hormone and Pituitary Program, NIDDK). Cultures were incubated for 48 hours at 37° C. and proliferation was evaluated by the addition of 0.5 µCi of ³H-thymidine for four hours followed by harvesting and scintillography. When stimulated with PRL alone, Nb2 cells yield sigmoid shaped growth curves that plateau at approximately 2 ng PRL/ml.

Example 4

Generation and Expression of CypB-NT Mutant

CypB-NT was generated by overlapping PCR mutagenesis. The forward CypB primer containing the Kpn1 Site and Kozak signal sequence was combined with the reverse primer (5'–3') AAATACACCTTGGCCGCAGAAGGTC-CCGG (SEQ ID NO: 6), while the reverse primer containing the Xho1 site was combined with the forward primer (5'–3') GCGGCCAAGGTGTATTTTGACCTACGAATTGGA (SEQ ID NO: 7). the resulting PCR products were purified, mixed and re-amplified with the forward and reverse CypB primers. Their resulting PCR product, lacking amino acid residues 2–12 of the mature peptide while retaining the leader sequence was confirmed by dideoxynucleotide sequencing. This PCR-derived mutant was digested, cloned into pAc5/V5-HisA, expressed in the *Drosophila* Expression Systems and purified as described in Example 1.

---

The invention claimed is:

1. A method of identifying test compounds that decrease somatolactogenic hormone-induced cell proliferation comprising contacting cyclophilin B with a somatolactogenic hormone in the absence and presence of the test compound in vitro, wherein a decrease in binding of cyclophilin B to the somatolactogenic hormone in the presence of the test compound as compared to binding in the absence of the test compound indicates that the test compound decreases somatolactogenic hormone-induced cell proliferation.

2. The method of claim 1 wherein the somatolactogenic hormone is prolactin.

* * * * *